United States Patent [19]

Feinstein

[11] 4,422,860

[45] Dec. 27, 1983

[54] ON-COLUMN CAPILLARY GAS CHROMATOGRAPHIC INJECTOR

[75] Inventor: Paul L. Feinstein, Berkeley, Calif.

[73] Assignee: Varian Associates, Inc., Palo Alto, Calif.

[21] Appl. No.: 342,958

[22] Filed: Jan. 26, 1982

[51] Int. Cl.³ .............................................. B01D 15/08
[52] U.S. Cl. .......................................... 55/67; 55/197
[58] Field of Search ................................... 55/67, 197

[56] References Cited

U.S. PATENT DOCUMENTS

| | | | |
|---|---|---|---|
| 3,920,420 | 11/1975 | Valentin et al. | 55/197 |
| 4,035,168 | 7/1977 | Jennings | 55/197 |
| 4,168,235 | 9/1979 | Guillemin et al. | |
| 4,269,608 | 5/1981 | Sisti et al. | 55/67 |
| 4,274,480 | 7/1981 | McGee | 55/67 |
| 4,356,733 | 11/1982 | Braunweiler | |

FOREIGN PATENT DOCUMENTS 2030055 4/1980 United Kingdom.
8001585 8/1980 United Kingdom.

OTHER PUBLICATIONS

M. Galli, et al., "Special Cooling System for the On–Column Injector in Capillary Gas Chromatography Eliminating Discrimination of Sample Compounds", J. High Res. Chrom. & Chrom. Communications, 2 366 (1979).
C. A. Cramers et al., "Direct Sample Introduction System for Capillary Columns", J. of Gas Chromatography, 6 577 (1968).
K. Grob, et al., "On–Column Injection on to Glass Capillary Columns", J. of Chromatography, 151 311 (1978).
K. Grob, Jr., "Factors Affecting the Accuracy and Precision of Cold on–Column Injections in Capillary Gas Chromatography", J. of Chromatography, 189 109 (1980).
K. Grob, "On–Column Injection onto Capillary Columns", Part 2, J. High Res. Chrom. & Chrom. Comm., p. 263 (Nov. 1978).

Primary Examiner—John Adee
Attorney, Agent, or Firm—Stanley Z. Cole; Gerald M. Fisher

[57] ABSTRACT

Apparatus and method for injection of samples directly onto a column in a gas chromatograph with injection occurring in a temperature controlled zone outside the oven. The apparatus combines a guide means and valve assembly in alignment with an injection and thermal transfer assembly. In the guide means and valve assembly a radial seal engages the injection means to seal the injection volume, thereby eliminating back flash. In the injection and thermal transfer assembly the capillary column is centered and held in fixed position within a duct means. Means is provided to lower the temperature of the capillary column to a temperature below the vaporization temperature of the liquid sample prior to injection. After injection, means is further provided to raise the temperature of the capillary column to a temperature above the volatilization temperature of the liquid sample to vaporize it and pass it into the capillary column.

The method of on-column injection of the present invention comprises inserting an injection means through a radial seal means to a point just above a valve, opening the valve, further inserting the injection means through the valve and into the end of that portion of the capillary column within the thermal transfer assembly and outside the oven of the gas chromatograph, injecting a liquid sample into the end of the capillary column while maintaining the column at temperature below the vaporization temperature of said liquid sample, withdrawing the injection means from the capillary column and the valve means, closing the valve means, withdrawing the injection means through the injector duct and the radial seal means, and heating said column within said temperature controlled zone to volatilize said sample and pass it into said column.

25 Claims, 7 Drawing Figures

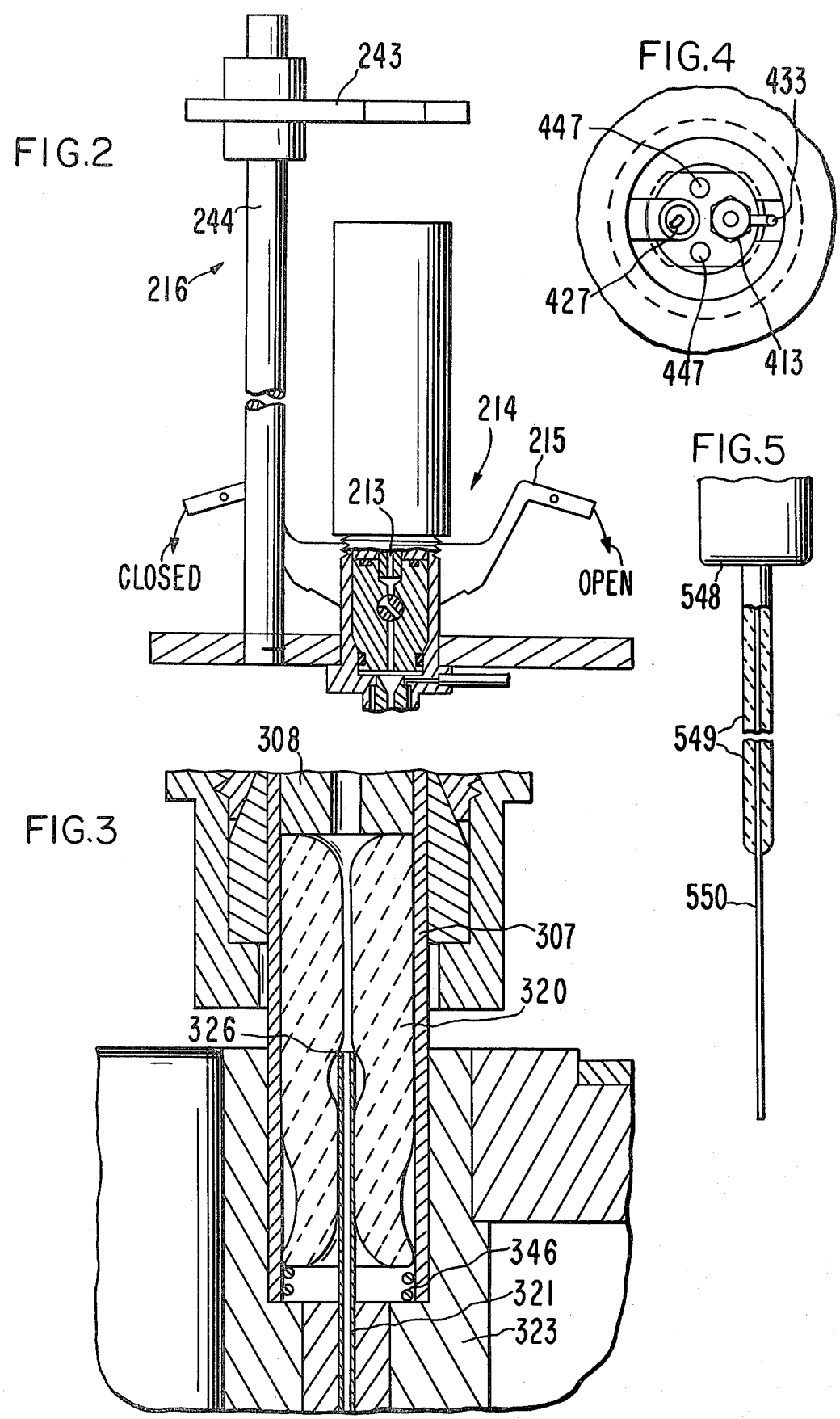

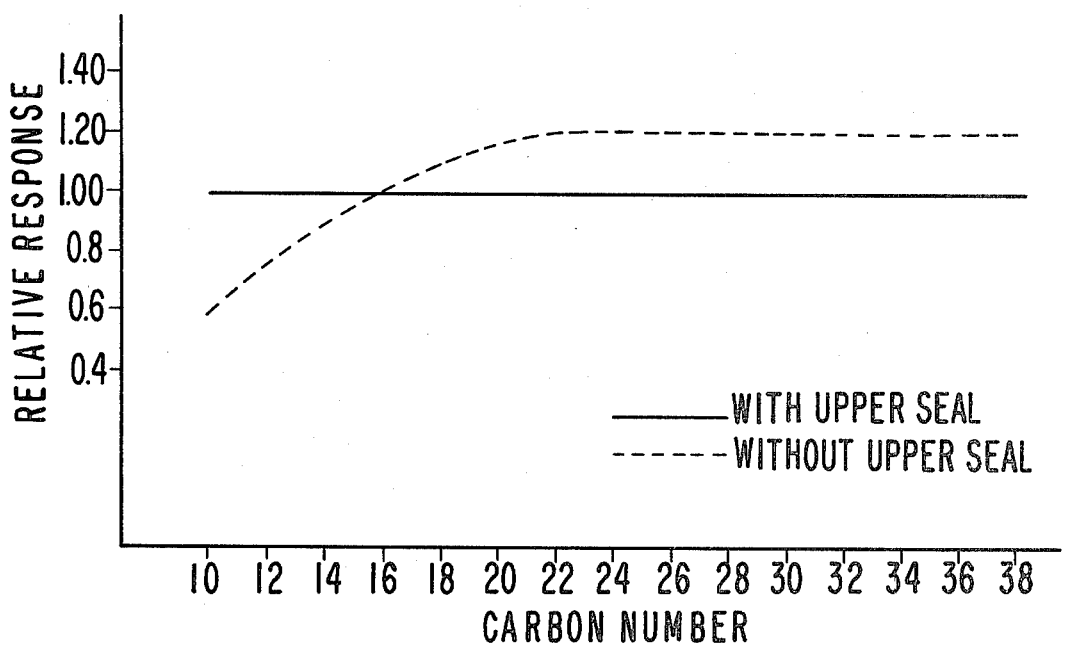
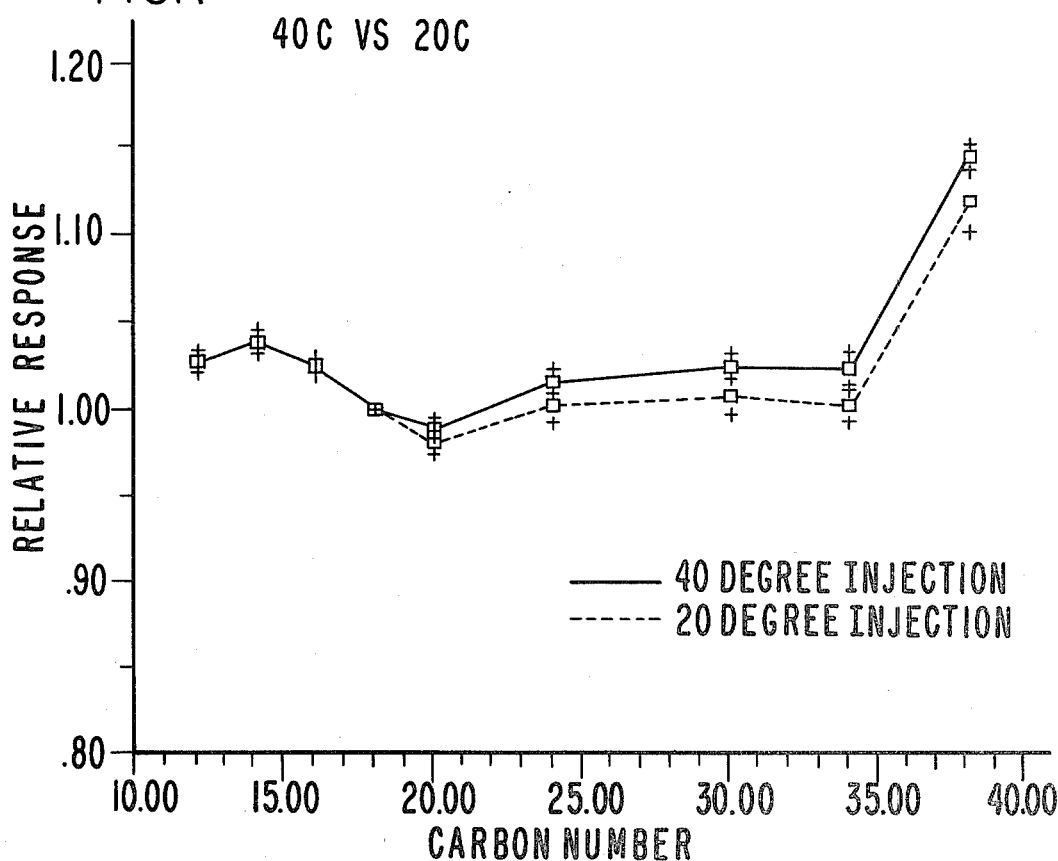

ON-COLUMN CAPILLARY GAS CHROMATOGRAPHIC INJECTOR

DESCRIPTION

1. Technical Field

This invention relates to an apparatus and method for performing on-column sample injection into a capillary gas chromatographic column under controlled temperature conditions outside the oven of the gas chromatograph.

2. Background Art

Gas chromatographs commonly employ an injector through which a sample is introduced, a heatable oven compartment, a column located principally inside the oven compartment for receiving the sample and for separating injected samples into their components, a carrier gas to sweep the sample through the column of the gas chromotograph, and a detector for detecting species as they exit from the column. Samples analyzed by gas chromatography may be liquid or gaseous. Liquids must, however, first be vaporized to produce dispersed droplets which can be swept through the column by the carrier gas.

Columns of increasingly smaller diameters have been used for gas chromatography. For example, standard (about 3.1 to about 6.5 mm internal diameter) columns are being replaced by capillary (about 0.18 to about 0.4 mm internal diameter) columns. As this occurs all major systems of the gas chromatograph must be redesigned to meet strict criteria such as low dead volume, increased resolution and the elimination of sources of baseline instabilities. On-column capillary injectors must provide accurate means for introducing sample into the column without loss due to spit back (also called backflash) of vaporized sample into the injector or injecting means (e.g., an autosampling device, a syringe, etc.), must avoid band broadening due to differential vaporization of the sample near the needle tip, and must also provide a continuous gas flow. With the advent of capillary column gas chromatography, the problems involving accurate injection, especially for decomposable or low boiling samples have been intensified due to the low sample volume requirements of capillary columns. To enable accurate injection of these types of samples into capillary columns without incurring band broadening, spit back or irregular gas flow more specific temperature profiles have become necessary for the injector.

The prior art in the area of cooled injections can be divided into two categories: cold trap or externally cooled injector. Cold traps have been used primarily to concentrate dilute samples outside of the injector prior to injection, or to eliminate solvents which might mask sample peaks. Once the sample is concentrated in the cold trap, it forms a plug which is heated to vaporize the sample and enable it to be carried by the carrier gas through the injector and into the column. Within the category of cooled injectors, samples have been injected into a pre-column, into a vaporization chamber, or directly into the column.

Use of a packed pre-column in the duct of a septum type injector is disclosed in C. A. Cramers, et. al., "Direct Sample Introduction System for Capillary Columns", *J. Gas Chromatography*, v. 6, page 577 (1968). There, a packed pre-column was inserted in front of the capillary column to allow vaporization of a sample, which had been injected into the precolumn packing, and removal from the solvent. Upon heating, the high boiling solvent remains in the pre-column and the vaporized (lower boiling) sample is swept into the column which connects to the lower portion of the injector. Surrounding the packed pre-column are both heating and cooling devices. The cooling device or shield utilizes a stream of liquid carbon dioxide during injection to trap the sample vapors as they flow out of the packed pre-column into the capillary column. The trapped sample is then heated using the heating device to allow the vapors to be carried together through the rest of the column by the carrier gas. The device does not inject samples directly into the column, and does not prevent spit back or back flash of sample. Injection in this case is a two-stage process in which the first stages involves vaporizing the sample and removing it from the solvent, then resolidifying it. With this approach, there is always the opportunity to vaporize some of the sample back into the upper portion of the injector; in addition, the discrete cold trap does not entirely trap the total sample injected.

The U.K. Patent Application of G. Sisti, et. al., "Vaporization Injector for Gas Chromatographic Columns", U.K. Pat. No. 2,039,777A, discloses use of a chamber between the syringe needle and the capillary column for sample vaporization. The sample is introduced into a heated chamber in which it vaporizes and is carried into either the column or a splitter device by the carrier gas. Carrier gas is introduced around the upper portion of the syringe needle, prior to its point of entry into the vaporization chamber, to minimize vapor pressure inside of the syringe needle. As shown in FIG. 2 of the Sisti '777A U.K. application, cool air is also introduced into an accessory mounted around the injection channel leading to the vaporization chamber. This cool air is introduced near the base of the accessory, is flowed through a hollow channel surrounding the injection channel, and thereafter flows out of the distal end of the hollow channel. This cooling sequence is designated as secondary cooling to distinguish it from external primary cooling. There is no disclosure of on-column injection, of precise temperature control of the area around the syringe needle, or of means to prevent either spit back or differential sample vaporization.

Secondary cooling has also been disclosed for use with on-column injection; see G. Sisti, et. al., "Method and Device for Sample Injection Under Controlled Conditions of Temperature Profile Into Gas Chromatographic Columns", U.S. Pat. No. 4,269,608, and M. Galli, et. al., "Special Cooling System for the On-Column Injector in Capillary Gas Chromatography Eliminating Discrimination of Sample Compounds", *J. High Res. Chrom. & Chrom. Comm.* 2, 366 (1979). In the '608 patent, the syringe needle is inserted into an injector duct to a point just above a rotary valve, the injector duct being open to the air, and the valve is opened and the needle inserted through the valve into a portion of the gas chromatographic column just inside the oven. In addition to passive cooling produced by fins or active cooling produced by coolant forced through coils around the portion of the column external to the oven, this patent shows the same type of secondary cooling shown in the U.K. '777A application. The term "secondary cooling" appears to be needed to distinguish from this type of passive or active cooling which is applied externally to the injector portion of the column. The benefits of combining secondary with primary cooling include effective trapping of sample compounds during injection into the portion of the column just inside the oven without the need to interfere with the operation of the oven. However, the structure does not eliminate the problems of carrier gas flow fluctuations on opening the rotary valve, of temperature fluctuations in the oven due to influence of the secondary cooling, of spit back of sample during injection, does not eliminate the inherent limitation of time necessary to heat the column due to the cylindrical sleeve which permits secondary cooling and does not permit temperature programming since the oven temperature is fixed insofar as injection is concerned.

The technique of injection of the sample into the column inside the oven raises the problem of differential vaporization of sample in the needle. This danger is present in the general approach of on-column injection as taught by K. Grob, et. al., "On-Column Injection on to Glass Capillary Columns", J. Chrom. 151, 311 (1978). The solution offered by Galli, et. al. to the Grob primary cooling/injection into oven problem, is the secondary cooling device as shown in the U.S. '608 patent and the U.K. '777A application referenced above. Incidentally, a gradual temperature gradient exists during injection between the hot oven and the cold injector which helps prevent suction of the sample upwards between the syringe needle and the capillary column wall by capillary action.

In K. Grob, Jr., "Evaluation of Capillary Gas Chromatography for Thermolabile Phenylurea Herbicides", J. Chrom. 208, 217 (1981), the problem of band broadening (or poor peak shape) due to differential elution of samples in gas chromatographic columns is presented. Generally, samples introduced into a cooled injector should be heated rapidly to introduce the sample into the column as a discrete entity. If heating is prolonged, the time band over which a particular constituent may be detected may be broadened, thereby, producing poor peak shapes. Such dispersal may also result when elution takes too long a period of time. It is shown that for phenylureas, the degradation of diuron depends on the elution temperature and the retention time. Since retention time depends on column length and carrier gas flow rate, the shorter the column and the higher the carrier gas flow rate, the shorter the retention time and the less the degradation. In addition, it is shown that the lower the elution temperature, the less the degradation. The problem with cooled on-column injectors, therefore, is to obtain reduction of band broadening and to obtain good peak shapes.

DISCLOSURE OF THE INVENTION

It is accordingly one object of the present invention to provide temperature controlled introduction of liquid samples into that portion of a capillary gas chromatographic column external to a gas chromatographic oven.

A further object of the present invention is to provide a method for on-column injection of samples into that portion of a capillary gas chromatographic column external to a gas chromatographic oven.

A further object of the present invention is the ability to perform an on-column capillary gas chromatographic injection cycle without unduely interrupting or fluctuating the carrier gas flow.

A further object of the present invention is the introduction of carrier gas flow above the sample introduction point to improve peak shapes by minimizing dead volume.

An additional object of the present invention is to provide apparatus and method for on-column injection in combination with means for temperature programming.

An even further object is to provide for uninterrupted carrier gas flow during the injection cycle by providing a sealing means at the top of the injector duct to provide a radial seal between the sample injection means and the injector duct.

An even further object is to provide a sheathed syringe needle to provide greater neelde strength, to prevent damage to the needle during injection, and to aid in forming an airtight seal between the needle and the injector duct during injection.

An even further object of the present invention is to provide a low dead volume injector duct insert to center the injection means and to reduce or eliminate scratching, chipping, or cracking of the end of the column portion extending outside of the gas chromatographic oven area.

SUMMARY OF THE INVENTION

Apparatus and method for injection of samples directly onto a column in a gas chromatograph with injection occurring in a temperature controlled zone outside the oven permits temperature control of injection, minimizes spit back, prevents differential sample vaporization and carrier gas flow fluctuations, and permits precise control of column temperature inside the gas chromatographic oven. The apparatus combines a guide means and valve assembly in alignment with an injection and thermal transfer assembly. In the guide means and valve assembly a radial seal engages the injection means to seal the injection volume, thereby eliminarting back flash. In the injection and thermal transfer assembly the capillary column is centered and held in fixed position within a duct means. Prior to injection, the capillary column is maintained at a temperature below the vaporization temperature of the liquid sample. After injection, the column is heated to at least the vaporization temperature of the liquid sample. The point of injection into the column is thus located within a controlled temperature zone outside the oven of the gas chromatograph.

The method of on-column injection of the present invention comprises inserting an injection means through a radial seal means to a point just above a valve, opening the valve, further inserting the injection means through the valve and into the end of that portion of the capillary column within the thermal transfer assembly and outside the oven of the gas chromatograph, injecting a liquid sample into the end of the capillary column while maintaining the column at temperature below the vaporization temperature of said liquid sample, withdrawing the injection means from the capillary column and the valve means, closing the valve means, withdrawing the injection means through the injector duct and the radial seal means, and heating said column within said temperature controlled zone to volatilize said sample and pass it into said column.

BRIEF DESCRIPTION OF THE DRAWINGS

For a more complete understanding of the apparatus and method of the present invention, reference may be made to the accompanying drawings which are incorporated herein by reference and in which:

FIG. 2 illustrates an alternate guide means and valve assembly;

FIG. 3 is a detailed axial section of one embodiment of the injector duct insert area of the injection and thermal transfer assembly;

FIG. 4 is a fragmentary elevational view of the injector of the present invention taken along lines 4—4 of FIG. 1;

FIG. 5 represents one embodiment of an injection means for use with the present invention;

FIG. 6 is a graph illustrating the responsiveness of the on-column injector to a range of carbon numbers with and without the upper radial seal; and FIG. 7 is a graph illustrating the responsiveness of the on-column injector of the present invention to a range of carbon numbers for two temperatures of injection.

DESCRIPTION OF THE PREFERRED EMBODIMENTS

Figure 1:
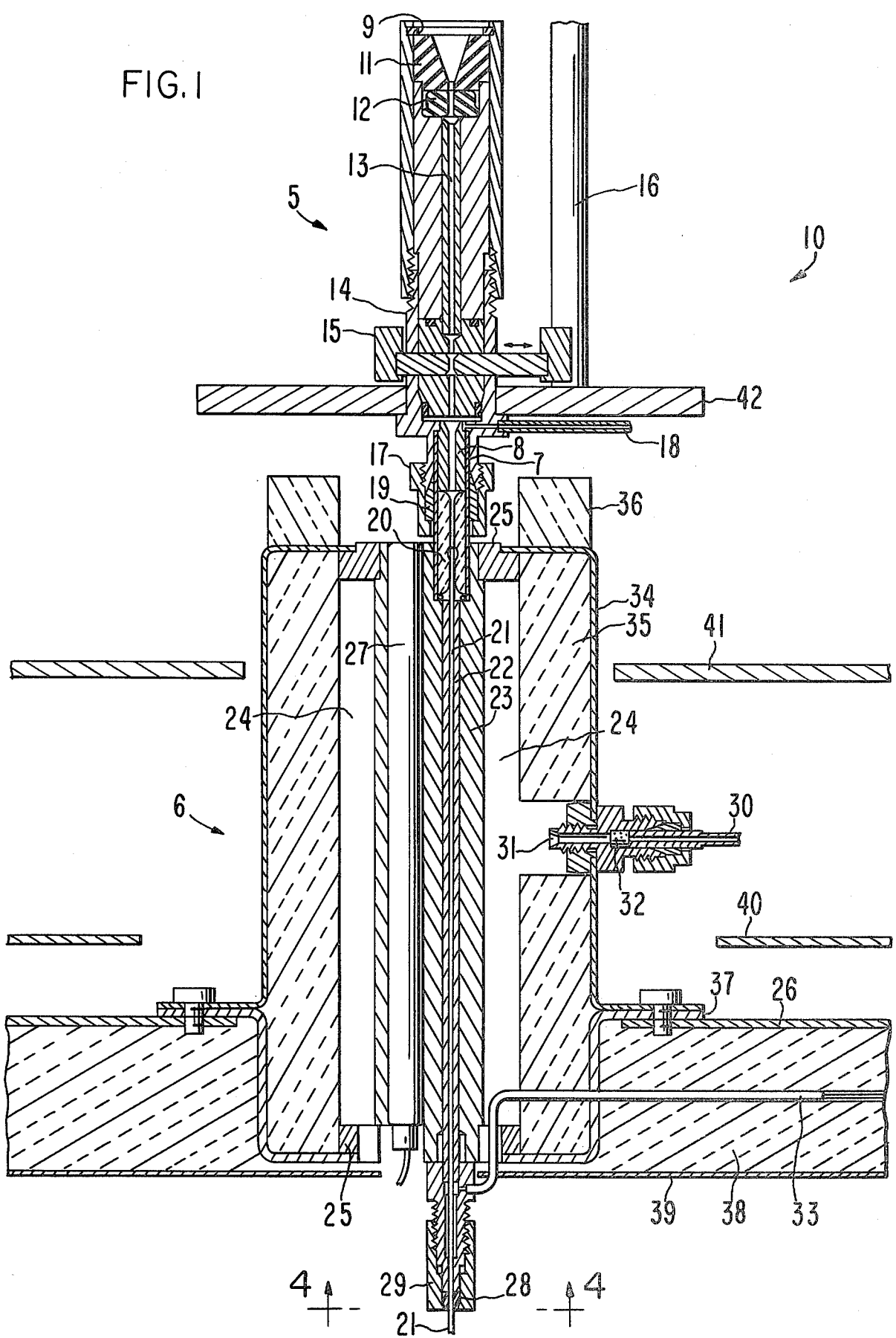
FIG. 1 represents an axial section of the injection of the present invention, shown here as a two-piece unit consisting of a guide means and valve assembly 5 and an injection and thermal transfer assembly 6 which are connected by nut 17.

The present on-column injector invention 10 comprises a guide means and valve assembly 5 and an injection and thermal transfer assembly 6. Together they function to produce reliable on-column injection even of labile compounds. To minimize poor peak shapes for labile compounds, separate controls are provided for the on-column injector and the oven of the gas chromatograph. In this way the heating rate for the on-column injector can be optimized for a particular sample and the column heating rate in the oven can be separately optimized for speed of analysis and column efficiency.

To prevent any possible fluctuations in carrier gas flow through the injector and column when the injector duct is opened to admit the injection means, the present invention provides, in addition to a valve means, a radial seal device to engage the injection means. Escape of sample and/or carrier gas out the top of the injector, and around the needle (called spit back or back flash) is thus eliminated by use of an air tight system. Thus, the introduction of the injection means (e.g., syringe needle, automatic sampling device, etc.) becomes a two-step process; the first step is insertion through the radial seal and the second step is insertion through the valve.

Even in a sealed system such as that of the present invention, some samples in the column will volatilize, fill the volume of the injector and not be totally transferred to the column during the gas chromatographic run. This loss can be minimized by controlling the initial temperature of the injector. On-column injectors of the prior art do not use precise control of the cooling air supply. The injector of the present invention uses a positively controlled coolant system which can maintain the injector at temperatures as low as $-60°$ C. The temperature can then be programmed upwards as desired to accommodate the characteristics of the sample and obtain complete and distinct injection directly into the column.

Further, the injector of the present invention has a minimum dead volume which is continually swept by carrier gas entering immediately below the inlet valve. This arrangement allows accurate injection of compounds with a carbon chain as low as 8 without the peak shape problems exhibited in the prior art.

The design of the on-column injector of the present invention with its minimal mass and separation from the column oven allows rapid heating of the injector. The ability to rapidly heat the injector to high temperatures allows higher molecular weight compounds to quickly exit the column in a band, thus resulting in low discrimination of these compounds.

Utilizing the on-column injector of the present invention, temperature control for sample introduction is accomplished outside of the oven with temperature controls which are separate from those used to regulate column temperature. Also, no cooling air flows into the oven area so that oven temperature can be set precisely.

STRUCTURE

The guide means and valve assembly 5 of FIG. 1 includes an injection means guide 16 (further described with reference to FIG. 2), and a radial seal 12. Radial seal 12 provides an airtight seal between the injecting means, for example a syringe needle or auto sampling means, and the injector duct 13. Radial seal 12 is preferably composed of a thermoplastic material. The radial seal 12 of the present invention is not a normally closed septum, but rather is a thermoplastic material which does not provide a seal until the sample introduction means is inserted through it. A septum, on the other hand, is known in the art to be a self-sealing membrane of elastomeric material which can be punctured to allow entry of a device such as a syringe needle into an area of different temperature, pressure, composition, etc., and reseals upon exit of the device to maintain the temperature, pressure, etc., difference. Seal cap 11 preferably made of stainless steel, is predrilled, holds radial seal 12 in place, and provides initial guidance for insertion of the injecting means into injector duct 13. Seal cap 11 may be provided with a clip ring 9 to provide slight pressure to keep radial seal 12 in position.

Valve body 14 holds a valve 15 in place. Valve 15 is shown as a slide-in, slide-out valve. A rotary valve as shown in FIG. 2 or other valve design known in the art may also be used. Radial seal 12 and valve 15 are used together to form an airtight seal which allows introduction of a sample into the capillary column 21 without loss of carrier gas or change of rate in the carrier gas flow. This is especially important for low boiling point or easily decomposable samples since carrier gas flow is constrained to be down into and around the column and there is no upward avenue of escape for volatile components.

Carrier gas is introduced through carrier gas line 18 and flows through spacer 8, injector duct insert 20 and into column 21. When valve 15 is closed, the carrier gas does not enter injector duct 13; when valve 15 is open and the injector means is in place, the carrier gas enters above spacer 8 and is stopped by radial seal 12 and prevented from escaping into the atmosphere. Carrier gas flow can be either flow or pressure controlled. Flow control of the carrier gas may be preferred for resolution and peak shape especially when temperature programming is used in the oven area. Flow control also permits the use of hydrogen as a carrier gas which is preferred for certain applications. Pressure control of the carrier gas may be preferred in other cases, especially in cases of isothermal oven operation.

Column 21 is positively held within injector and thermal transfer assembly 6, the region within the confines of and slightly above metal housing 34. Nut 17 grips and presses ferrule 19 against guide means and valve assembly connector tube 7. Injector duct insert 20 serves to center and receive column 21 and is typically fabricated from stainless steel, plastic, glass or similar material; preferably glass, is employed. Injector duct insert 20 is shaped so that the lower portion has a sufficient diameter to receive column 21 and the upper portion has a diameter narrower than the column 21 to thereby provide a positive termination for column 21. In one embodiment, shown in FIGS. 1 and 3, a bulb-like opening is provided to permit definite point of contact between column 21 and the bottom of the upper portion. The differential diameters of the lower and upper portions of injector duct insert 20 permits injection without scratching, chipping, or cracking of the column, or bending of the injection means. Nut 29 presses against ferrule 28 to thereby grip and seal column 21 at the bottom of injector 10. Column insert 22, a cylinder whose bore will accommodate column 21 and which is preferably made of stainless steel, is used within injector and thermal transfer assembly 6 to assist in column alignment and to provide rapid heat transfer between column 21 and heater block 23. Heater block 23 is shown to be a cylindrically-shaped metal body having high thermal conductivity, preferably copper, which provides rapid thermal transfer between column 21 and any thermal transfer medium within plenum 24. Preferably, heater block 23 has a low thermal mass. Purge outlet line 33 is available to remove carrier gas and possible sample or solvent vapor contamination from the injector between chromatographic runs.

Injection occurs in that portion of column 21 between the bottom of injector duct insert 20 and the junction with purge outlet line 33 and preferably occurs in that portion of column 21 between the bottom of injector duct insert 20 and the point of insertion through outer oven wall 26. Control of the temperature of the injection area of injector 10 is accomplished by providing a flow of fluid, preferably liquid $CO_2$ into plenum 24, and by supplying heat from heater cartridge 27. Thus, injection occurs in a temperature controlled zone within injection and thermal transfer assembly 6. When cooling is accomplished, the selection of the fluid is in part determined by the temperature range required for minimizing volatility of sample and solvent components. The cooling fluid is admitted through tubing 30, metering frit 32 and nozzle 31. This cooling fluid circulates through cooling plenum 24 and escapes to the outside through the insulation and through openings between plenum 24 and the injector body. Metering frit 32 permits an accurate control of the rate of flow of cooling fluid. Metering frit 32 is also used to obtain a high pressure drop, thus enabling a phase change from liquid to gas. Ceramic washers 25 are located at the top and bottom of cooling plenum 24 and isolate it thermally.

Heater cartridge 27 may be of a resistive element type known in the art and is placed in communication with heater block 23. Heater cartridge 27 and heater block 23 are designed with low thermal mass to be capable of heating the column area with sufficient rapidity to achieve good peak shapes for the organic compounds being detected. For example, 200° C./minute has been found to be a heating rate which provides satisfactory peak shapes for samples of molecular composition up to $C_{60}$. Heat sink 42 is used to thermally isolate the upper and lower portions of injector 10.

The temperature of column 21 is measured using thermocouples, thermistors or the like known in the art. At least one temperature measuring device 447 is inserted into heater block 23 at a point adjacent column 21 and heater cartridge 27 to measure temperature. The preferred placement of the temperature measuring device as shown in FIG. 4 eliminates temperature overshoot and dead bands.

Control of heater cartridge 27 within the temperature controlled zone is achieved with electrical components known in the art. The temperature controller system should be capable of flexible temperature programming. That is, the rate of increase of temperature should be easily adjustable according to the type of compound being injected. The injector temperature controller should be separate from that for the oven to provide optimum temperature control to each. Because, in general, the optimum heating rate increases with molecular weight, it should be possible with this system to create a heating ramp curve of complex form, matching and optimum for a specific compound or sample, which could be programmed by the operator.

Injection and thermal transfer assembly 6 of on-column injector 10 is enclosed within metal housing 34. Insulation 35 is placed between housing 34 and cooling plenum 24. Additional external insulation 36 can be used to surround the region of the injector duct insert 20, if needed, to control temperature. Metal housing 34 is attached to the gas chromatographic oven wall 26 by means of flanges 37. Portions of injector 10 may extend into the insulation 38 between the outer oven wall 26 and the inner oven wall 39. However, there is no cooling fluid flow inside the gas chromatographic oven area due to the presence of ceramic washer 25. Baffle 40 and injector cover 41 may be employed to provide further temperature stability to injection and thermal transfer assembly 6.

FIG. 2 shows one embodiment for an injection means guide and an alternate embodiment for the valve closure for the injector duct. In this figure, valve 214 employs valve actuator 215 of the rotary or rocker type for opening or closing injector duct 213. Injection means guide 216 is one embodiment of a device for aiding insertion of the injection means into injector duct 213. In this embodiment a swing arm 243 is provided with a hole large enough to admit a syringe needle, but small enough to stop a syringe barrel. Arm 243 swivels on post 244 to allow the syringe needle to be inserted into injector duct 213. Injection means guide 216 provides support during injection for the injection syringe and provides an external reference point for the position of the tip of the injection syringe in injector duct 213.

An expanded view of one embodiment of the injector duct insert area is shown in FIG. 3. In this view the central region of the inner surface of injector duct insert 320 describes a bulb-like shape to provide a sharp point of contact 326 for capillary column 321. The angled shape of this inner surface of injector duct insert enables good contact between the insert and columns of various diameters. The outside surface of injector duct insert 320 rests in, but is not necessarily concentric with the injector duct. An axially bored spacer 308 is provided at the top of the injector duct insert area to enable easier centering of the injection means into the injector duct insert and to reduce the dead volume of this area. A spring 346 can be used below injector duct insert 320 to provide resilience to injector duct insert 320 when capillary column 321 is introduced. Spring 346 may be supported on heater block 323.

FIG. 4 is a fragmentary elevational view of the injector of the present invention taken from direction 4—4 of FIG. 1. Two thermocouple or resistance wells 447 are provided in heater block 27. In operation, one or both of these wells will be in use. This figure also shows the heater cartridge 427, injector duct 413 and purge outlet line 433.

One embodiment of the injection means used with the present invention is shown in FIG. 5. The injection means comprises a syringe body 548, a syringe needle 550 and a sheath 549 which covers, supports and is sealed onto a portion of needle 550. Injection into capillary columns necessarily involves the use of small diameter needles 550. These needles are easily subject to being bent or to breaking. One way to reduce such damage is to decrease the length of the needle. A short needle is provided for the injector of the present invention by sheathing the majority of the needle with a ceramic or plastic material. This is desirable so that the only portion of the fragile needle 550 which is exposed is that length required to penetrate column 326. Sheathing 549 extends between syringe barrel 548 and the exposed portion of needle 550 and serves to provide a seal when inserted into the radial seal 12 of FIG. 1 to thereby close the injector duct to air prior to opening of the valve and insertion of the injection means into the capillary column. Using such a sheathed needle, the exposed portion of the needle 550 is reduced to a minimum.

METHOD OF OPERATION

The on-column injector of the present invention enables easy injection of samples onto capillary gas chromatographic columns under temperature controlled conditions. Prior to injection of a sample, the temperature controller (not shown) is set to bring the heater block 23 to a suitably low temperature, such that the most volatile components in the sample are not lost. In FIG. 7, the effect of inlet temperature on sample discrimination by carbon number shows that a lower temperature produces less volitilization. A response factor of 1.0 indicates that preferential volatilization of sample components has not occurred.

The injection process first involves inserting the injecting means, for example a syringe, through the radial seal 12 and seal cap 11 to a point just above valve 15. Such positioning of the injection means above valve 15 can be accomplished by using an injecting means guide 16 to indicate externally the height of the needle above the valve. The second step of the injection process is the opening of the valve 15 and insertion of the injecting means through the remaining length of injector duct 13, through axially bored spacer 8, through injector duct insert 20, and then into capillary column 21. The syringe needle 550 (see FIG. 5) is physically introduced inside capillary column 21, but need not travel much beyond the upper end of the column. Once sample is injected into column 21 within the temperature controlled zone of injection and thermal transfer assembly 6, the injecting means is withdrawn from the column, out through injector duct insert 20 and finally out through valve 15. Valve 15 is then closed and the injecting means is withdrawn completely from guide and valve means 5 of injector 10 out through radial seal 12 and seal cap 11. After injection is accomplished, the temperature of the heater block 23, and column 21, is rapidly brought up to a temperature suitable for vaporizing the injected sample. Temperature programming may be employed to optimize performance. When the temperature of the column initial section is rapidly raised, the chromatographic process begins; this event is syncrhonized electrically with the initial point on the chromatograpby data system. This synchronization is accomplished through the signal which actuates the temperature controller.

It has been found that the rate of this rapid temperature rise is a significant factor in both sample integrity and peak shapes on the chromatograph. In general, for organic compounds, the greater the molecular weights, the faster the temperature rise necessary to achieve narrow, undistorted peak shapes. For instance, for samples containing $C_{40}$ components, a temperature rise of 180° C./min is necessary. For lower molecular weight components, a slower rate is more optimum. The ideal temperature ramp is one which starts out slowly and increases in time. Such a hyperbolic or multistage injector heating rate would be a desirable feature of an on-column injector and achievable by having the injector decoupled from the oven, as occurs with the present invention. It has also been found that certain important compounds such as phenylureas are subject to thermal decomposition when subjected to an overly rapid heating rate. Control of the initial rise in temperature, therefore, is an important variable for these compounds, and the facility to decouple the initial temperature from the rise in temperature experienced in the oven contributes to more optimum chromatographic performance. See, e.g., K. Grob, Jr., "Evaluation of Capillary Gas Chromatography for Thermolabile Phenylurea Herbicides", J. Chrom. 208, 217, (1981).

What is claimed is:

1. An injector for introduction of a liquid sample directly into a capillary gas chromatographic column, the point of injection within said column being enclosed within a temperature controlled zone, comprising:
   means for heating said column within said temperature controlled zone to at least the vaporization temperature of said sample during a portion of the injection cycle, said temperature controlled zone being located outside the oven of said gas chromatograph;
   means for maintaining said column within said temperature controlled zone at a temperature below the vaporization temperature of said liquid sample while said liquid sample is introduced through the end of said column directly to said point of injection;
   duct means for holding said end of said gas capillary column, said duct means serving to fix and stabilize said column to thereby permit liquid samples to be introduced directly into said column at said point of injection; and
   sealing means within said duct means for enabling introduction of said liquid sample without fluctuation in the carrier gas flow.

2. An injector in accordance with claim 1 wherein said means for enabling introduction comprises a valve positioned within said duct means to be opened during said introduction of sample and to be closed during the injection cycle to prevent fluctuations in carrier gas flow.

3. An injector in accordance with claim 2 wherein said means for enabling introduction further comprises septumless sealing means located at the upper end of said duct means.

4. An injector in accordance with claim 3 in combination with injection means to introduce sample into said column and wherein said septumless sealing means forms a radial seal with said means used for sample introduction.

5. An injector in accordance with claim 4 wherein said injection means comprises a syringe having a sheathed needle, the diameter of said sheath being selected to sealingly engage with said radial septumless seal.

6. An injector in accordance with claim 2 wherein said valve is actuated by slideable movement.

7. An injector in accordance with claim 2 wherein said valve is actuated by rotary movement.

8. An injector in accordance with claim 1 in which said duct means for holding said column includes an injector duct insert for alignment of said column in said duct means.

9. An injector in accordance with claim 8 in which said injector duct insert has a central opening along its length for receiving said end of said column, said central opening having an angled inner surface which serves to positively stop said end of said column.

10. An injector in accordance with claim 9 wherein said inner surface of said injector duct insert forms a bulb-shaped cavity so that said end of said column fits into said cavity and terminates against a wall of said cavity.

11. An injector in accordance with claim 9 wherein the external shape of said injector duct insert conforms closely to the shape of the internal surface of said duct means.

12. An injector in accordance with claim 9 wherein said injector duct insert is fabricated from glass.

13. An injector in accordance with claim 1 in which the length of said capillary column which extends outside said oven of said gas chromatograph is about 3 inches.

14. An injector in accordance with claim 1 wherein said means for maintaining said column within said temperature controlled zone at a temperature below the vaporization temperature comprises a cylindrical plenum extending around at least a portion of said length of said column.

15. An injector in accordance with claim 14 in combination with means for introducing cooled gas to said cylindrical plenum to produce coaxial flow through said plenum.

16. An injector in accordance with claim 1 wherein said means for heating said column within said temperature controlled zone comprises a heating cartridge extending along at least a portion of the exterior of said duct means.

17. An injector in accordance with claim 1 in combination with means to provide flow control for the carrier gas being introduced to said gas chromatograph.

18. An injector in accordance with claim 1 in combination with means to provide pressure control for the carrier gas being introduced to said gas chromatograph.

19. A method for on-column injection of liquid samples directly into a capillary gas chromatographic column, the point of injection within said column being enclosed within a temperature controlled zone, comprising:

fixing the end of said capillary column within a duct means;

inserting an injection means into said duct means, said duct means including radial seal means and valve means, said insertion being accomplished through said radial seal means to a point above said valve means;

opening said valve means;

inserting said injection means through said valve means further into said duct means;

inserting said injection means into said end of said capillary column to a point of injection within said column, said column being held within said duct means within a temperature controlled zone outside of the oven of said gas chromatograph so that injection occurs within said temperature controlled zone;

lowering the temperature in said temperature controlled zone to below the vaporization temperature of said liquid sample;

injecting a liquid sample into said capillary column at said point of injection;

withdrawing said injection means from said capillary column;

withdrawing said injection means through said valve means;

closing said valve means;

withdrawing said injection means through said injector duct;

withdrawing said injection means through said radial seal means; and raising the temperature in said temperature controlled zone to volatilize said liquid sample and pass it into said column.

20. A method for on-column injection in accordance with claim 19 wherein said step of opening said valve means comprises the step of sliding a slideable valve means.

21. A method for on-column injection in accordance with claim 19 wherein said step of opening said valve means comprises the step of rotating a rotary valve means.

22. A method of on-column injection in accordance with claim 19 wherein said step of raising the temperature in said temperature controlled zone is accomplished by the step of programming an increase in temperature in said temperature controlled zone in accordance with a specified time-temperature profile.

23. A method for on-column injection in accordance with claim 19 wherein said step of inserting said injection means through said valve means into the end of said capillary column includes the step of inserting said injection means into an injector duct insert which aligns both said injection means and said capillary column.

24. A method for on-column injection in accordance with claim 19 wherein said step of inserting said injection means through said radial seal comprises the step of inserting a syringe having a sheathed needle through said radial seal to form a seal between said radial seal and said sheath.

25. A method for on-column injection in accordance with claim 24 wherein said step of inserting an injection means through a radial seal to a point just above a valve means includes the step of guiding the downward movement of said syringe by a fixed external guide.

* * * * *